(12) United States Patent
Gill

(10) Patent No.: US 10,278,954 B2
(45) Date of Patent: May 7, 2019

(54) METHOD OF TREATING A CNS DISORDER USING A WATER-SOLUBLE HISTONE DEACETYLASE INHIBITOR

(71) Applicant: RENISHAW PLC, Gloucestershire (GB)

(72) Inventor: Steven Streatfield Gill, Bristol (GB)

(73) Assignee: RENISHAW PLC, Wotton-Under-Edge (GB)

( * ) Notice: Subject to any disclaimer, the term of this patent is extended or adjusted under 35 U.S.C. 154(b) by 88 days.

(21) Appl. No.: 15/422,090

(22) Filed: Feb. 1, 2017

(65) Prior Publication Data

US 2017/0216256 A1    Aug. 3, 2017

(30) Foreign Application Priority Data

Feb. 1, 2016   (GB) .................................. 1601773.3

(51) Int. Cl.
| | | |
|---|---|---|
| A61K 31/40 | (2006.01) | |
| A61K 31/4045 | (2006.01) | |
| A61K 9/00 | (2006.01) | |
| A61K 9/107 | (2006.01) | |
| A61K 31/19 | (2006.01) | |
| A61K 31/555 | (2006.01) | |
| A61K 39/00 | (2006.01) | |
| A61K 45/06 | (2006.01) | |
| A61K 47/10 | (2017.01) | |

(52) U.S. Cl.
CPC ........ *A61K 31/4045* (2013.01); *A61K 9/0085* (2013.01); *A61K 9/1075* (2013.01); *A61K 31/19* (2013.01); *A61K 31/555* (2013.01); *A61K 39/0011* (2013.01); *A61K 45/06* (2013.01); *A61K 47/10* (2013.01)

(58) Field of Classification Search
CPC .................................................. A61K 31/4045
See application file for complete search history.

(56) References Cited

FOREIGN PATENT DOCUMENTS

| WO | 2007/024841 A2 | 3/2007 |
| WO | 2013/135727 A1 | 9/2013 |
| WO | 2013/166487 A1 | 11/2013 |
| WO | 2014/016591 A1 | 1/2014 |
| WO | 2015/180865 A1 | 12/2015 |

OTHER PUBLICATIONS

Zhou et al (Cancer J. Jan.-Feb. 2012; 18(1) 1-22).*
FEBS J., vol. 281, 2014, Maleszewska, M., et al., "HDAC inhibitors are potential regulators of tumor growth and tumor microenvironment," pp. 302-303.
White, E., et al., "A phase I trial of carboplatin administered by convection-enhanced delivery to patients with recurrent/progressive glioblastoma multiforme," Cont. Clin. Trials, vol. 33, 2012, pp. 320-331.

(Continued)

*Primary Examiner* — Benjamin J Packard
(74) *Attorney, Agent, or Firm* — Oliff PLC

(57) ABSTRACT

A method of treating a CNS disorder. The method comprises providing a water-soluble histone deacetylase inhibitor, and administering the water-soluble histone deactylase inhibitor directly into a brain via convection enhanced delivery.

24 Claims, 9 Drawing Sheets
(5 of 9 Drawing Sheet(s) Filed in Color)

(56) References Cited

OTHER PUBLICATIONS

Grasso, C.S., et al., "Functionally-defined Therapeutic Targets in Diffuse Intrinsic Pontine Glioma," Nature Med., vol. 21, pp. 555-559, Jun. 2015.

Nakagawa, H., et al., "Abstract 3143: Sodium butyrate induced cellular senescence, inhibited invasion and modulated cellular metabolism in glioblastoma cell," Cancer Res., vol. 74, p. 3143, Oct. 1, 2014.

Alvarez, A. A., et al., "The Effects of Histone Deacetylase Inhibitors on Glioblastoma-Derived Stem Cells," J. Mol. Neurosci., vol. 55, pp. 7-20, 2015.

Lee, E., et al., "Interim Analysis of a Phase I/II Study of Panobinostat in Combination with Bevacizumab for Recurrent Glioblastoma (IN10-1.005)," Neurology, vol. 80, No. 7, Mar. 22, 2013.

Lee, E., et al., "Phase I Study of Vorinostat in Combination with Temozolomide in Patients with High-Grade Gliomas: North American Brain Tumor Consortium Study 04-03," Clin. Cancer Res., vol. 18, pp. 6032-6039, Nov. 1, 2012.

Iwamoto, F.M., et al., "A phase I/II trial of the historine deacetylase inhibitor romidepsin for adults with recurrent malignant glioma: North American Brain Tumor Consortium Study 03-03", Neuro-Oncol., vol. 13, pp. 509-516, Mar. 3, 2011.

Atadja, Peter, "Development of the pan-DAC inhibitor panobinostat (LBH589): Successes and challenges", Cancer Letters, vol. 280, pp. 233-241, 2009.

Morrison, P.F., et al., "High-flow microinfusion: tissue penetration and pharmacodynamics", Am J Physiol Regul Integr Comp Physiol, vol. 266, pp. R292-R305, 1994.

West, Alison, et al., "The anticancer effects of HDAC inhibitors require the immune system", OncoImmunology, vol. 3, pp. e27414-1-e27414-3, 2014.

KiBem, Kim, et al., "Eradication of metastatic mouse cancers resistant to immune checkpoint blockade by suppression of myeloid-derived cells", PNAS, vol. 111, No. 32, pp. 11774-11779, Aug. 12, 2014.

Bobo, R. Hunt, et al., "Convection-enhanced delivery of macromolecules in the brain", Proc. Natl. Acad. Sci. USA, vol. 91, pp. 2076-2080, Mar. 1994.

Oct. 20, 2016 Search Report issued in Great Britain Patent Application No. 1601773.3.

* cited by examiner

METHOD OF TREATING A CNS DISORDER USING A WATER-SOLUBLE HISTONE DEACETYLASE INHIBITOR

This application claims priority to Great Britain Application No. 1601773.3, filed Feb. 1, 2016. The entire contents of the prior application are hereby incorporated by reference herein in their entirety.

TECHNICAL FIELD

The application relates to water-soluble histone deacetylase inhibitors for use in treating CNS disorders, wherein the water-soluble histone deacetylase inhibitor is to be administered via convection enhanced delivery (CED).

BACKGROUND

Convection Enhanced Delivery

Many promising therapeutic agents for central nervous system (CNS) disorders have failed to attain clinical success due to the blood-brain barrier (BBB), which prevents the passage of agents from the systemic circulation into the brain. Systemic administration of high drug doses may increase delivery to the brain, but this approach risks significant side effects and toxicity. Direct delivery of drugs to the brain facilitates bypass of the BBB. However, the therapeutic efficacy of drugs injected into the brain parenchyma and/or tumours is limited by minimal diffusion from the site of injection and consequently, small volumes of distribution. In 1994, the concept of convection-enhanced (CED) delivery was introduced as a solution to these obstacles to therapeutic drug delivery to the CNS (Bobo R H, Laske D W, Akbasak A, Morrison P F, Dedrick R L, Oldfield E H, Convection-enhanced delivery of macromolecules in the brain. *Proc Natl Acad Sci USA*, 91:2076-80 (1994); Morrison P. F., Laske D. W., Bobo H., Oldfield E. H., Dedrick R. L., High-flow microinfusion: tissue penetration and pharmacodynamics. *Am J Physiol.*, 35: R292-305 (1994)).

CED describes continuous infusion of agents under pressure through neurosurgically-placed micro-catheters. This method has several potential advantages over conventional drug delivery methods. CED facilitates highly accurate anatomical targeting, delivery of higher (therapeutic) drug concentrations throughout clinically relevant volumes of brain tissue or tumour, and reduces systemic side effects. CED has been extensively investigated in the context of a wide range of CNS disorders in both pre-clinical and clinical trials—most notably for the treatment of brain tumours and Parkinson's disease.

Drugs can be administered directly to the brain in concentrations that would result in significant toxicity if given systemically. In contrast to delivery techniques that are dependent on diffusion, such as intraparenchymal injection, which leads to drug distribution heterogeneously over short distances down a concentration gradient; CED enables the controlled, homogeneous distribution of drugs over many centimeters of brain, regardless of the molecular size of the drug (Morrison et al.), Furthermore, as CED leads to the displacement of extracellular fluid with infusate, it offers an unparalleled opportunity to manipulate the extracellular environment of malignant brain tumours such as glioblastoma multiforme (GBM) and diffuse intrinsic pontine glioma (DIPG).

CED has been investigated in the context of a wide range of brain disorders, in both pre-clinical and clinical trials—most notably for the treatment of Parkinson's disease or tumours at other sites within the brain. It has been shown to be safe, and effective in delivering agents to specific anatomical sites, and significant beneficial effects have been seen, including tumour response to chemotherapy, and re-growth of putaminal neurons leading to reversal of Parkinsonism.

Intermittent CED can be used to repeatedly administer drug by CED to the same target area without the need for further surgery. This is especially useful when treating malignant tumours, as repeated exposure to chemotherapy is essential to ensure that cells are adequately exposed to drug.

Histone Deacetylase Inhibition in CNS Disease

DNA and histones provide the main building blocks for nucleosomes, the structural units of chromatin that are important for packaging DNA. Changes in the structural configuration of chromatin to an active (open) or inactive (condensed) form alters the accessibility of DNA for transcription, ultimately affecting gene expression. One of the major ways that transcription factor binding to DNA is regulated is through changes in chromatin conformation, which in turn is governed by chemical modifications such as the acetylation and deacetylation of lysine residues of core nucleosomal histones. These changes are under the control of opposing activities of histone deacetylase (HDAC) and histone acetylase (HAT), and lead to altered gene expression, including genes involved in cell cycle regulation, differentiation and apoptosis. Acetylation is generally linked to an 'open' chromatin state that is ready for transcription or that corresponds to actively transcribed genomic regions, whereas deacetylation is associated with a closed or inactive state, leading to gene repression. The relative degree of histone acetylation and deacetylation therefore controls the level at which a gene is transcribed. HDAC also has crucial roles in cell cycle proliferation and apoptosis, including transcription factors such as p53, NF-jB and E2F1, which play key roles in tumorigenesis and anti-tumor response, as well as proteins that do not directly regulate gene expression but instead regulate DNA repair (Ku70), the cellular cytoskeleton (a-tubulin) and protein stabilisation (Hsp90). Notably, among non-histone HDAC substrates, Hsp90 plays a major role in the proper folding and stability of several major oncoproteins. HDAC activity also regulates cell protein turnover via the aggresome pathway, which if disrupted, results in the accumulation of polyubiquitinated misfolded protein aggregates, leading to cell stress and caspase-dependent apoptosis. These observations have extended the mechanism of anti-tumor activity of panobinostat and other HDAC inhibitors (HDACi) to include effects on non-histone proteins, implicated in multiple oncogenic pathways, in conjunction with epigenetic changes (Ataja, Development of the pan-DAC inhibitor panobinostat (LBH589): successes and challenges. *Cancer Lett.* 280:233-241 (2009)).

As well as having anti-cancer properties, HDACi, such as panobinostat but also including sodium valproate, veronostat, trichostatin A and others, interact with the host immune system. They have been shown experimentally to promote the systemic cytokine and effector response of cytotoxic T cells and have far less efficacy in immunodeficient animals. Indeed, it seems that an intact immune system is necessary for their function (West, Smyth, Johnstone, The anticancer effects of HDAC inhibitors require the immune system. *Oncoimmunology* 3(1):e27414)(2014)). Panobinostat has immunoregulatory effects in patients with Hodgkin's lymphoma through the modulation of serum cytokine levels and T-cell co-stimulatory molecules such as PD-1. Panobinostat has also been reported to up-regulate MHC expression and sensitise tumour cells to immune-mediated cell death in malignant melanoma. HDAC inhibition may therefore be particularly effective in malignancies that are poorly immunogenic and are associated with an immunosuppressive microenvironment, such as malignant glioma. There is recent pre-clinical evidence in mice that combining systemic HDACi with systemic immune checkpoint blockade is particularly effective in a mouse model of metastatic disease (Kim, Skora, Li, Liu, Tam, Blosser, Diaz, Papadopoulos, Kinzler, Vogelstein, Zhou, Eradication of metastatic mouse cancers resistant to immune check point blockade by suppression of myeloid-derived cells. *Proc Natl Acad Sci USA* 111:11774-9 (2014)).

It was found that water-soluble formulations of histone deacetylase inhibitors are particularly effective in treating CNS disorders when delivered directly to the brain by CED, especially when the CED is administered intermittently and/or in combination with chemotherapy or immunomodulatory agents.

SUMMARY

Disclosed embodiments provide direct delivery of water-soluble formulations of histone deacetylase inhibitors to the brain. Direct delivery of water-soluble formulations of histone deacetylase inhibitors preferably refers to administration by convection enhanced delivery (CED). Preferably the CED is administered intermittently via a chronic implantable drug delivery system. This approach can be combined with both systemic and directly (e.g. via CED) administered chemotherapy and/or immunomodulatory agents for the treatment of central nervous disease, including glial malignancies (such as Glioblastoma multiforme (GBM) and Diffuse intrinsic pontine glioma (DIPG)) and non-malignant inflammatory and neurodegenerative disease of the brain.

However, many histone deacetylase inhibitors are water-insoluble and are therefore not suitable for use by direct administration to the brain parenchyma by CED. Drugs need to be formulated in a water-soluble medium, via encapsulation or other methods using non-toxic excipients.

The inventors have demonstrated that a water-soluble formulation comprising a water-insoluble histone deacetylase inhibitor encapsulated in a micelle is active against rat and human glioma cells. The water-soluble formulation distributes well through white and gray matter of the brain and does not induce neuronal or synaptic toxicity. CED administration of the water-soluble formulation has been found to prolong the survival of tumour bearing rats.

In a first aspect, disclosed embodiments provide a water-soluble histone deacetylase inhibitor for use in treating CNS disorders, wherein the water-soluble histone deactylase inhibitor is to be administered directly into the brain via convection enhanced delivery (CED). Also provided are methods of treatment of CNS disorders comprising directly administering a water-soluble histone deacetylase inhibitor into the brain via CED.

Water-soluble histone deacetylase inhibitors may cross the blood brain barrier, but this may only be achievable at toxic systemic doses. However, direct administration to the brain of water-soluble histone deacetylase inhibitors will permit high local concentrations of drug without causing systemic toxicity.

Indeed, it was demonstrated that water-soluble histone deacetylase inhibitors are toxic toward cancer cells in a dose dependent manner and that a water-soluble histone deacetylase inhibitor will potentiate the effects of a chemotherapeutic agent, such as carboplatin, indicating a synergistic enhancement of cytotoxicity. It was also demonstrated that when compared over the same period, a greater than therapeutic dose of water-soluble histone deacetylase inhibitor is less toxic to neuronal cells than a relatively low therapeutic dose of chemotherapeutic agent.

Water-soluble histone deacetylase inhibitors can be administered to the brain by CED in an intermittent regime. The inhibitors may be combined with systemic therapy that may augment their effect, or vice versa. Systemic therapy may include conventional chemotherapy, or immunomodulatory agents, such as immune checkpoint blockers.

The disclosed embodiments additionally provide a water-soluble histone deacetylase inhibitor for use in treating glioma, wherein the water-soluble histone deacetylase inhibitor is to be administered systemically and concurrently with CED of a chemotherapeutic agent. Preferably the water-soluble histone deacetylase inhibitor is valproate and the chemotherapeutic agent is carboplatin.

DETAILED DESCRIPTION

The disclosed embodiments provide water-soluble histone deacetylase inhibitors for use in treating CNS disorders, wherein the water-soluble histone deactylase inhibitor is to be administered via convection enhanced delivery (CED). Also provided are methods of treatment of CNS disorders comprising directly administering a water-soluble histone deacetylase inhibitor into the brain via CED. The CNS disorder may be cancer, preferably brain cancer, more preferably glioma, including GBM and/or DIPG.

The water-soluble histone deacetylase inhibitor may be a water or lipid soluble histone deacetylase inhibitor encapsulated in a lipid membrane carrier such as a liposome, micelle or in a nanoparticle. Alternately, the water or lipid soluble histone deacetylase inhibitor may be encapsulated in a polymeric carrier such as a polymeric nanoparticle or dendrimer. Polymeric nanoparticles include polymer micelles, which may be formed from pluronic block co-polymers composed of, for example, poly (ethylene oxide) (PEO) and poly (propylene oxide) (PPO). In embodiments, water or lipid soluble histone deacetylase inhibitor may be encapsulated in a pluronic F127 micelle.

Preferably, the lipid membrane or polymeric carrier has sustained drug release properties. In other words, the lipid membrane or polymeric carrier may provide controlled release of the water-soluble histone deacetylase inhibitor in order to increase the half-life of the water-soluble histone deacetylase inhibitor in tissue. The lipid membrane or polymeric carrier may also be biodegradable and is preferably non-neurotoxic. Suitable lipid membrane or polymeric carriers for use in the disclosed embodiments have a diameter of about 10 to about 500 nm, preferably about 10 to about 300 nm. More preferably the lipid membrane or polymeric carriers for use in the disclosed embodiments have a diameter of 200 nm or less. In preferred embodiments, the lipid membrane or polymeric carriers have a neutral surface charge.

Suitable lipid soluble histone deacetylase inhibitors for use in the disclosed embodiments include, but are not limited to, panobinostat, Entinostat, Vorinostat, Mocetinostat, Romidepsin, Belinostat, Abexinostat, Givinostat, Resminostat, Quisinostat, Pracinostat, Pyroxamide, Tubacin and Trichostatin A, or combinations thereof. Preferably the lipid soluble histone deacetylase inhibitor is panobinostat.

Suitable water-soluble histone deactylase inhibitors for use in the disclosed embodiments include, but are not limited to, sodium valproate, sodium butyrate and dacinostat, or combinations thereof. Preferably the water-soluble histone deacetylase inhibitor is sodium valproate (also known as valproic acid). Such water-soluble histone deacetylase inhibitors can be administered into the brain via CED without the need for encapsulation in a lipid membrane or polymeric carrier.

Typically the water-soluble histone deacetylase inhibitor is to be administered daily to a patient via CED for a period of about 4 to about 12 hours. The water-soluble histone deacetylase inhibitor may be for administration daily for at least 1 day, or at least 2 days, or at least 4 days via CED. Daily administration typically refers to administration on sequential days. The water-soluble histone deacetylase inhibitor may be for administration in repeat cycles of 4-6 week intervals.

The water-soluble histone deacetylase inhibitor may be administered in combination with artificial cerebrospinal fluid (aCSF). ACSF as used in the disclosed embodiments may comprise glucose, proteins and ionic constituents. Preferably the aCSF comprises NaCl at a similar concentration to that found in natural CSF, that is to say the concentration is preferably within 15%, more preferably within 10% of the concentration in natural CSF. Preferably the aCSF comprises $NaHCO_3$ at a similar concentration to that found in natural CSF, that is to say the concentration is preferably within 15%, more preferably within 10% of the concentration in natural CSF. Preferably the aCSF comprises KCl at a similar concentration to that found in natural CSF, that is to say the concentration is preferably within 15%, more preferably within 10% of the concentration in natural CSF. Preferably the aCSF comprises $NaH_2PO_4$ at a similar concentration to that found in natural CSF, that is to say the concentration is preferably within 15%, more preferably within 10% of the concentration in natural CSF. Preferably the aCSF comprises $MgCl_2$ at a similar concentration to that found in natural CSF, that is to say the concentration is preferably within 15%, more preferably within 10% of the concentration in natural CSF. The aCSF can comprise glucose at a similar concentration to that found in natural CSF, that is to say the concentration is within 15%, preferably within 10% of the concentration in natural CSF. In preferred embodiments, the aCSF may omit glucose, so as to reduce the likelihood of bacterial growth in any catheter used to administer the composition to a subject. Most preferably, the aCSF does not comprise glucose or proteins.

The water-soluble histone deacetylase inhibitor may be delivered via at least one chronically implanted CED catheter, especially an intraparenchymal catheter. The CED catheter may be a stepped catheter, i.e. having a cannula with a stepped outer diameter with the diameter of the step or steps decreasing from the proximal to the distal end, such as those described in WO2007/024841. Alternatively the CED catheter may be a recessed step catheter such as those described in WO2014/016591 which is incorporated herein by reference. Recessed step catheters comprise a distal section of tubing having an outer diameter that is smaller than the internal diameter of the catheter guide tube and arranged to create a recess for retaining brain tissue in the distal end section of the guide tube, between the guide tube and the distal section of tubing of the catheter. The retained brain tissue acts as a seal against reflux of fluid along the guide tube and catheter.

The water-soluble histone deacetylase inhibitor may be delivered via at least two chronically implanted CED catheters or via three or more of such catheters. Chronically implanted CED catheters refer to catheters that will be left in situ in the brain of a subject for at least six months, preferably for at least one year. Usually chronically implanted catheters will remain in place for the lifetime of a subject.

Preferably the water-soluble histone deacetylase inhibitor is delivered into gray matter of the brain such as the cerebral cortex and/or the putamen.

The water-soluble histone deacetylase inhibitor may be for administration in combination with a systemic dose of the same histone deacetylase inhibitor, which may be in a water-soluble or lipid soluble form. Administering the doses of histone deacetylase inhibitor in combination requires that the histone deacetylase inhibitor be present in the brain and the body of a patient at the same time. However, the systemic dose may be administered before, after or during administration of the dose delivered by CED into the brain. Preferably therapeutic levels of the histone deacetylase inhibitor are present simultaneously in both the brain and in the body of the patient.

The water-soluble histone deacetylase inhibitor may be administered in combination with a chemotherapeutic agent or another water-soluble histone deacetylase inhibitor. Preferably the chemotherapeutic agent is also to be administered via CED, while the other water-soluble histone deacetylase inhibitor may be administered systemically or via CED. As discussed above, administering the dose of water-soluble histone deacetylase inhibitor in combination with a chemotherapeutic agent or another water-soluble histone deacetylase inhibitor requires that these components be present in the brain and the body of a patient at the same time. However, the chemotherapeutic agent or other water-soluble histone deacetylase inhibitor may be administered before, after or during administration of the water-soluble histone deacetylase inhibitor delivered by CED into the brain. Preferably therapeutic levels of the components are present simultaneously in both the brain and in the body of the patient.

Suitable chemotherapeutic agents for use in the disclosed embodiments include, but are not limited to, carboplatin, topotecan, cisplatin, oxaliplatin, satraplatin, picoplatin, nedaplatin and triplatin, or combinations thereof. Preferably the chemotherapeutic agent is carboplatin.

The water-soluble histone deacetylase inhibitor may be administered to the brain via intermittent CED concurrently with systemic administration of a further therapeutic agent, such as an alkylating agent, an anti-cancer antibody and/or a steroid. Suitable alkylating agents include, but are not limited to, nitrogen mustards such as mechlorethamine, cyclophosphamide, ifosfamide, melphalan and chlorambucil; ethylenamine and methylenamine derivatives, such as altretamine and thiotepa; alkyl sulfonates, such as busulfan; nitrosoureas, such as carmustine and lomustine; triazenes, such as dacarbazine, procarbazine and temozolomide; and platinum-containing antineoplastic agents, such as cisplatin, carboplatin and oxaliplatin. Preferably the alkylating agent is temozolomide. Suitable anti-cancer antibodies may include, but are not limited to, bevacizumab and ramucirumab. Suitable steroids for systemic administration include, but are not limited to, corticosteroids, such as dexamethasone.

The water-soluble histone deacetylase inhibitor may be administered to the brain via intermittent CED concurrently with cranial radiotherapy, such as sterotactic radiotherapy.

The water-soluble histone deacetylase inhibitor may be administered to the brain via intermittent CED concurrently with an immune check point blockade. The immune check point blockade may include, but is not limited to, one or more of an anti PD-1 antibody (such as nivolumab) and an anti CTLA-4 antibody (such as ipilimumab).

The water-soluble histone deacetylase inhibitor may be administered to the brain via intermittent CED concurrently with immunotherapy, such as systemic glioma vaccination.

The water-soluble histone deacetylase inhibitor may be administered concurrently with systemic administration of a drug efflux inhibitor. The drug efflux inhibitor may include, but is not limited to, cyclosporin A, Verapamil, Quinidine, Dexverapamil, vaspodar, mitotane, lanquidar, elecridar or combinations of the same. Concurrent administration of a drug efflux inhibitor may have particular advantages in reducing the rate at which the water-soluble histone deacetylase inhibitor diffuses through the blood brain barrier, thereby maintaining higher concentrations of the water-soluble histone deacetylase inhibitor in the brain for longer periods of time.

The water-soluble histone deacetylase inhibitor may be administered at a concentration of from about 0.5 mM to about 100 mM, preferably about 1 mM to about 50 mM, more preferably about 2.5 mM to about 10 mM. In alternative embodiments, the soluble histone deacetylase inhibitor may be administered at a concentration of from about 0.5 nM to about 100 nM, preferably about 1 nM to about 50 nM, more preferably about 2.5 nM to about 10 nM.

Another embodiment provides a water-soluble histone deacetylase inhibitor for use in treating glioma (including GBM and DIPG), wherein the water-soluble histone deacetylase inhibitor is to be administered systemically and concurrently with CED of a chemotherapeutic agent. Suitable water-soluble histone deacetylase inhibitors and chemotherapy agents are as described herein. In a preferred embodiment, the water-soluble histone deacetylase inhibitor may be sodium valproate and wherein the chemotherapeutic agent may be carboplatin.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The disclosed embodiments are described with reference to the accompanying drawings in which.

EXAMPLES

Figure 1:
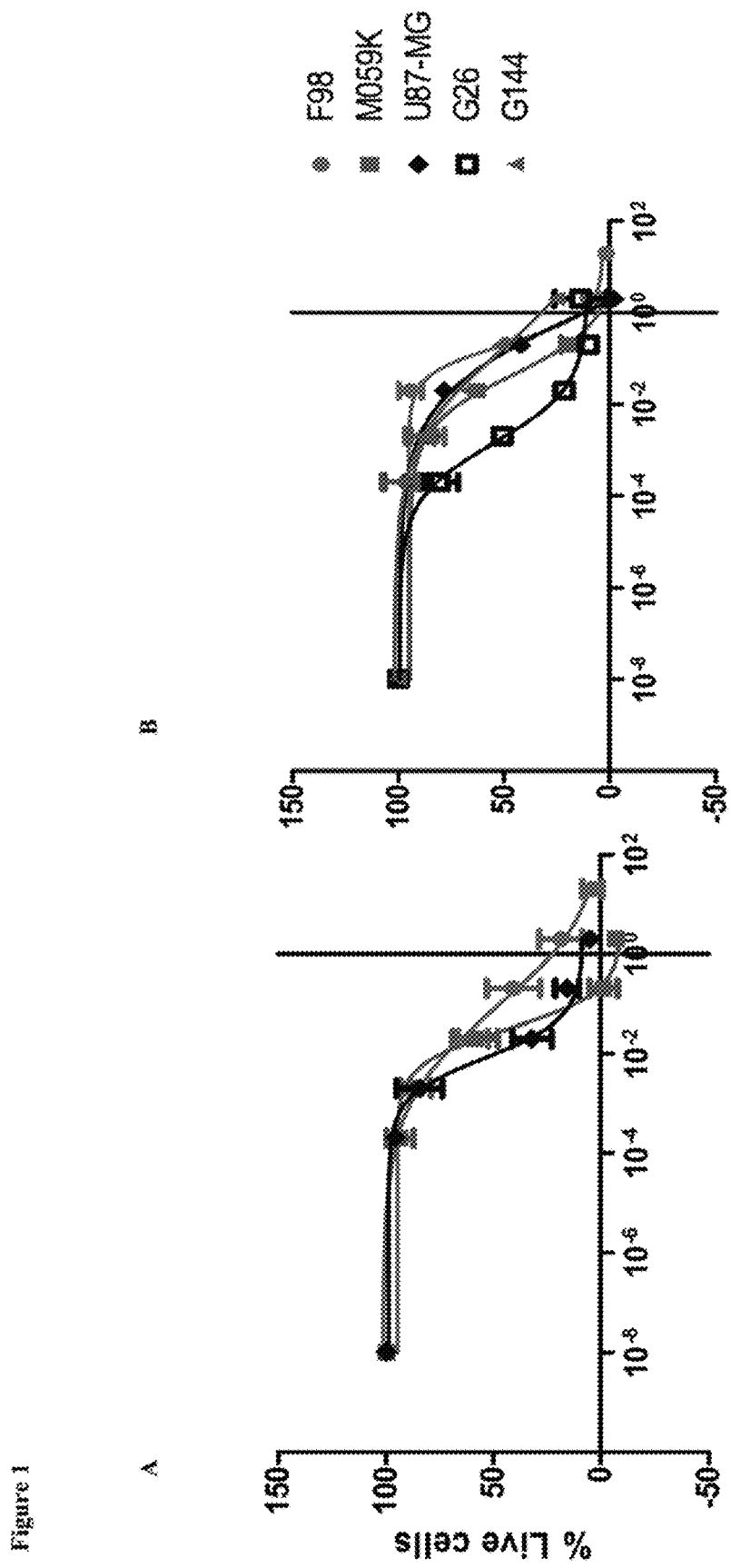
FIG. 1 shows the dose-response effect of micellar panobinostat (F127-PAN) in vitro. A) Rat F98, Human M059K and U87-MG glioma cells incubated F127-PAN for 72 hours. B) Cells (including G144 G26 glioma stem-like cells) washed with fresh media (drug removed) after 6 hours exposure and assays 72 hours later. % live cells measured using a fluorescent Live-Dead® assay (Invitrogen). All experiments performed in triplicate.
Figure 2:
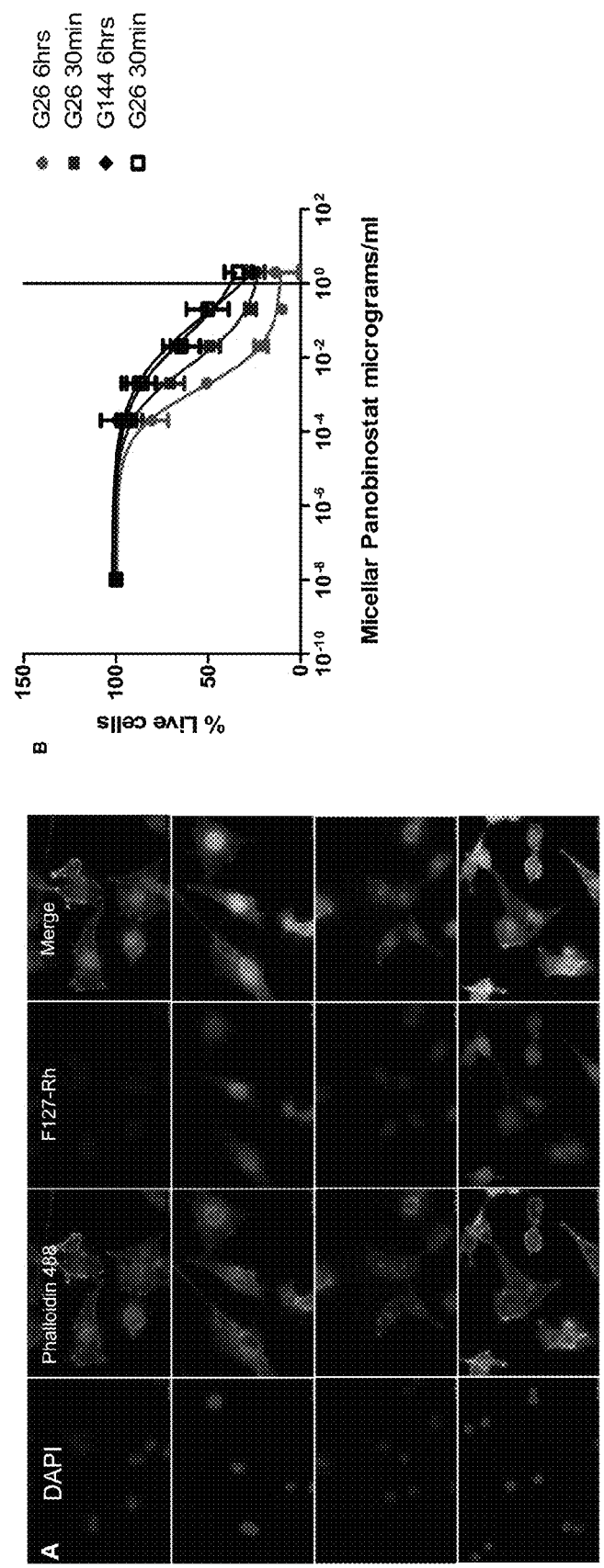
FIG. 2 shows A) Immunofluorescent microscopy of human U87-MG glioma cells with fluorescent 5% F127-aCSF micelles (F127-Rh) over time. Fluorescent polymer co-localises with the nucleus within 15 minutes of incubation. B) The in vitro dose-response effect of F127-PAN is almost identical in G144 and G26 glioma stem-like cells when they are exposed to drug for 6 hours or 30 minutes. Cell death assayed 72 hours after dosing.
Figure 3:
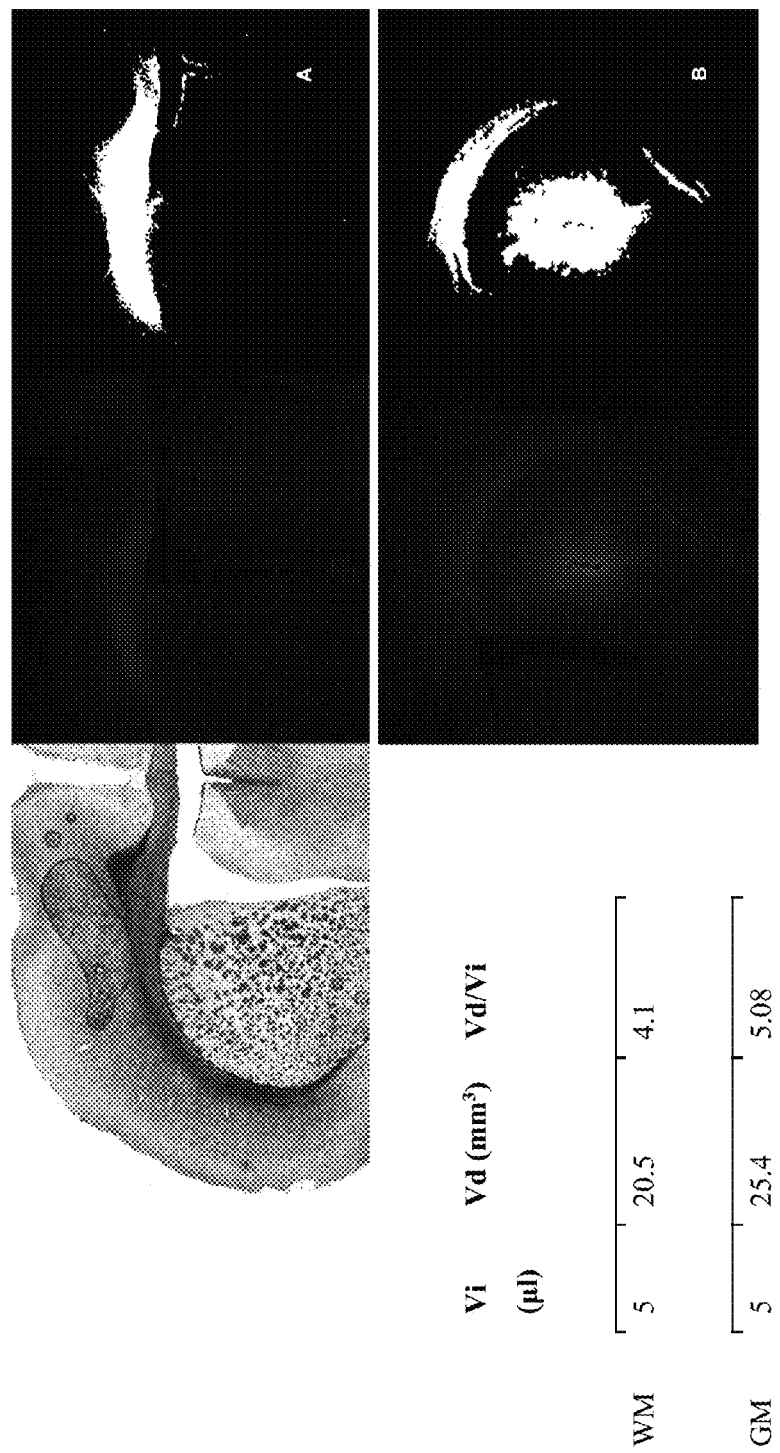
FIG. 3 shows distribution of rhodamine labelled fluorescent F127 (F127-Rh) micelles in rat white (A) and gray (B) matter (WM, GM) following acute stereotactic infusion by CED. Volume of distribution (Vd)/Volume of infusion (Vi) ratio 4:1 and 5:1 respectively.
Figure 4:
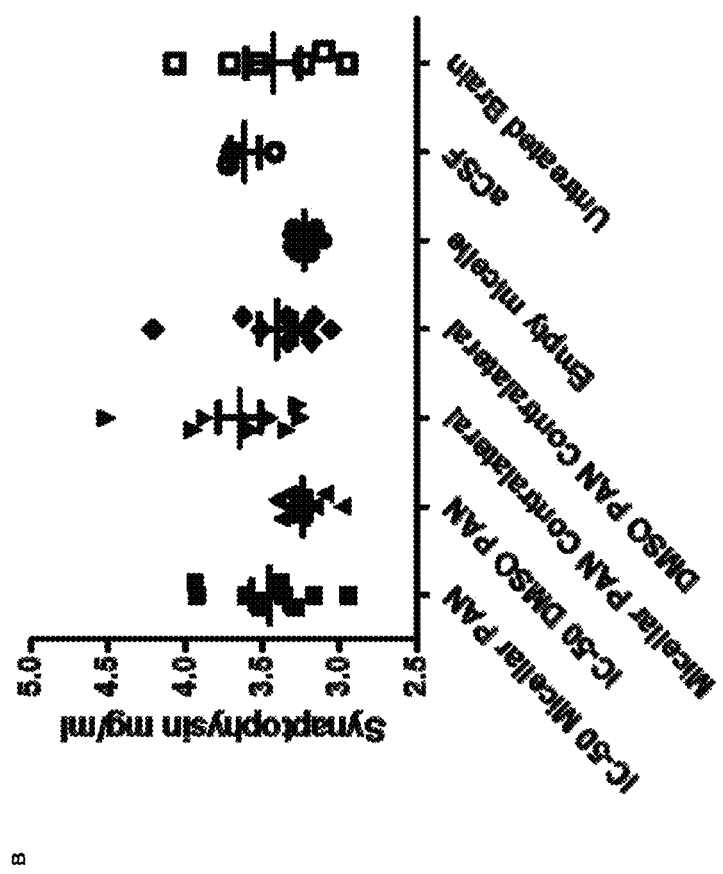
FIG. 4 shows in vivo toxicity assay of F127-aCSF and F127-PAN at the IC-50 dose for F98 cells after a 6 hour exposure (0.6 µg/ml). A) Immunofluorescent microscopy of fixed rat brain for neurons (NeuN) and glia (GFAP) 21 days after acute striatal infusion of 5 µl of either aCSF (control), F127-aCSF or F127-PAN. B) Synaptophysin ELISA of protein isolated from rat brain 21 days after infusion comparing F127-aCSF, F127-PAN and Panobinostat in DMSO against aCSF and untreated controls. No significant difference detected. (1 way ANOVA $p>0.05$).
Figure 4:
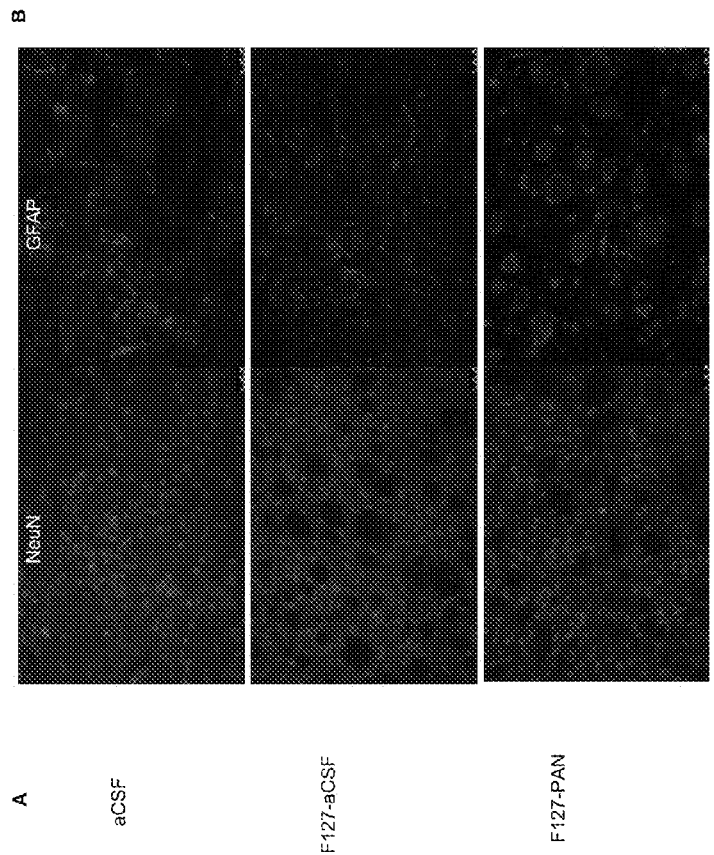
Figure 5:
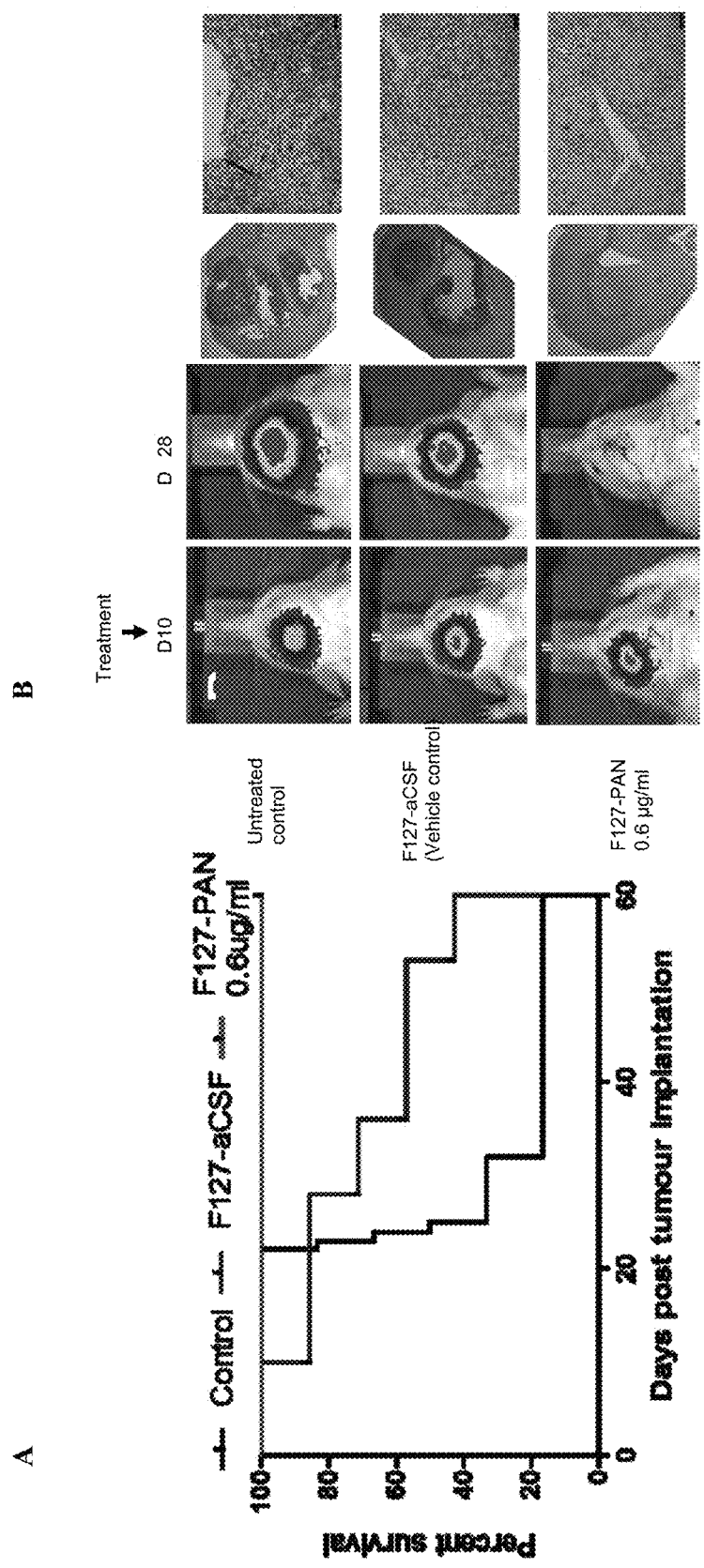
FIG. 5 shows the in vivo effect of F127-PAN (0.6 µg/ml) after a single administration by CED in the Fischer 344/F98-Luc orthotopic rat glioma model. Animals with visible tumour bioluminescence treated on day 10 after stereotactic implantation of 105 luciferase expressing F98 glioma cells into the left striatum. A) Kaplan-Meier survival analysis of a 60 day experimental period showing a significant survival advantage in treated animals compared to untreated and vehicle-only controls (n=21: 7 animals per group. Log-Rank $p=0.0001$). B) Bioluminescent imaging shows loss of transcranial bioluminescence in treated animals compared to controls (B1) and no evidence of tumour histologically post mortem (B2-haematoxylin & eosin).

Example 1: Convection Enhanced Delivery of a Water-Soluble Nano-Micelle Formulation Panobinostat. Summary of Pre-Clinical Results and Evidence as a Therapy for Malignant Glioma Aims
  Produce a water-soluble formulation of panobinostat, a pan-histone deacetylase inhibitor using self-assembling micelles formed from pluronic P407 (F127) in artificial CSF (aCSF).
  Determine the in vitro anti-glioma properties of micellar panobinostat in human and rat glioma using a cell viability assay.
  Investigate the distribution in white and gray matter of a fluorescent form of pluronic P407 (F127) micelles in a rat model of CED.
  Determine the toxicity of pluronic P407 (F127) micelles as a drug delivery tool when delivered to rat brain by CED using immunofluorescence microscopy and synaptophysin ELISA.
  Determine the toxicity of micellar panobinostat when delivered to rat brain by CED.
  Investigate the in vivo efficacy of micellar panobinostat in the Fisher 344/F98-luc glioma model.
Results
  Micellar panobinostat (F127-PAN) is active in vitro against both human and rat glioma cell lines, including glioma stem-like cells (see FIG. 1).
  Fluorescent F127 micelles (labelled with rhodamine—F127-Rh) co-localise to the nucleus after 15 minutes of exposure in vitro. The cytotoxic effect of F127-PAN is not different when comparing a 6 hour and 30 minute exposure to drug in vitro with glioma stem-like cells (see FIG. 2).
  Fluorescent F127 distributes in rat white and gray matter with a Volume of distribution (Vd) 4-5 times greater than the volume of infusion (Vi) (see FIG. 3).
  F127-PAN does not cause a change in neuronal staining in rat striatum 21 days after acute infusion by CED when compared to aCSF infusion. Infusion of drug does cause a difference in glial staining, suggestive of glial toxicity. There is no quantitative change in the concentration of synaptophysin between drug infused brain and vehicle only (F127-aCSF), aCSF and untreated controls (see FIG. 4).
  F127-PAN is active in vivo in the Fischer 344/F98-luc glioma model when administered by CED and is associated with a significant survival benefit compared to matched controls (see Table 1 and FIG. 5).

TABLE 1 survival benefit of F127-PAN administered via CED in the Fischer 344/F98-luc glioma model compared to matched controls

| Untreated | F127-aCSF | F127-PAN |
|---|---|---|
| Median survival (days) | | |
| 24.5 | 53 | — |
| % alive at 60 days | | |
| 16.7 | 42.9 | 100 |

Conclusions
  Micellar panobinostat is active against rat and human glioma cells including glioma stem like-cells in vitro.
  Pluronic P407 (F127) distributes well in rat white and gray matter when administered by CED acutely and is not toxic in single doses, and is an effective vehicle for this water-insoluble agent.
  Nano-micellar panobinostat does not show signs of neuronal or synaptic toxicity at the IC-50 dose when administered to rat brain by CED.
  The same dose of nano-micellar panobinostat is effective in prolonging the survival of glioma bearing rats when administered by CED as a single dose with histological evidence of anti-tumour effect.
  Intermittent CED of nano-micellar panobinostat may provide a novel treatment strategy for patients with malignant glioma.

Figure 6:
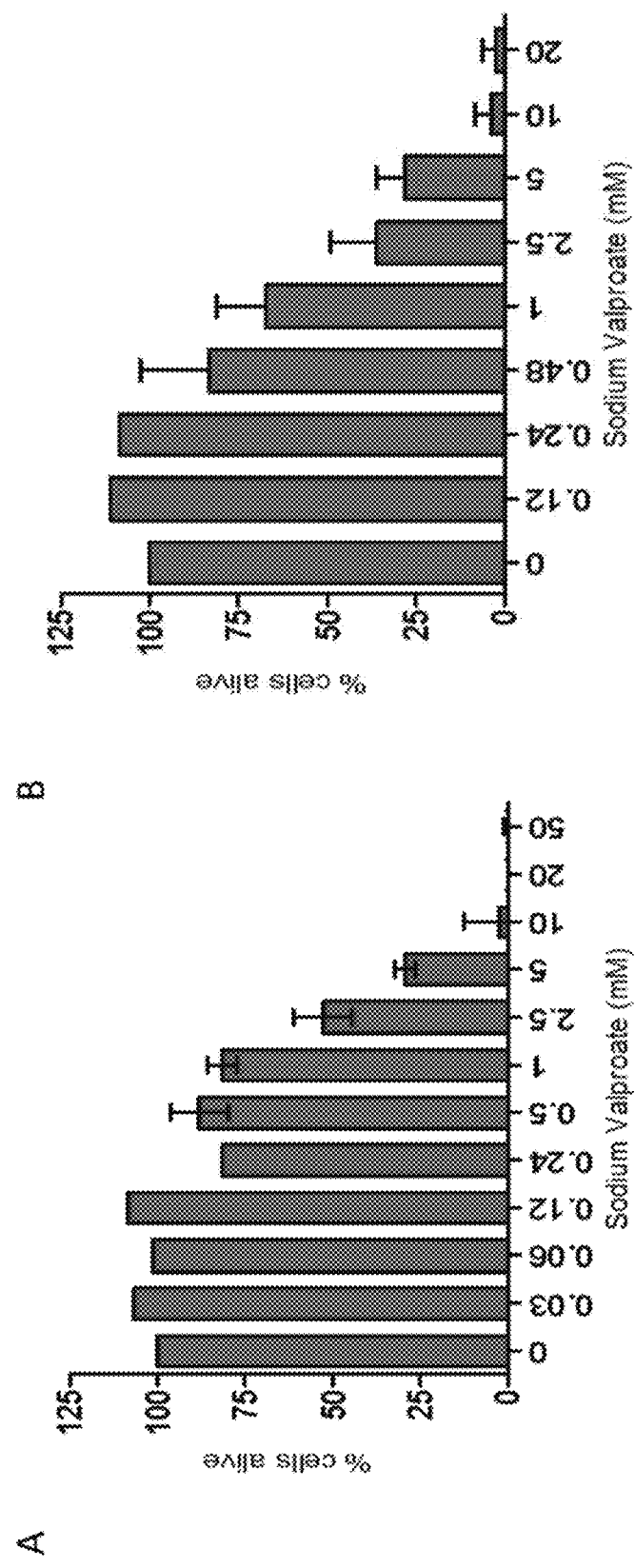
FIG. 6 shows that sodium valproate causes cytotoxicity to glioma cells in a dose dependent manner. Two independent glioma cell lines (A) SF7761 and (B) SF8628 were dosed with sodium valproate for 72 h, then subjected to an MTT assay to assess the effect of the drug on proliferation of glioma cells. Results are expressed as a % relative to untreated control.
Figure 7:
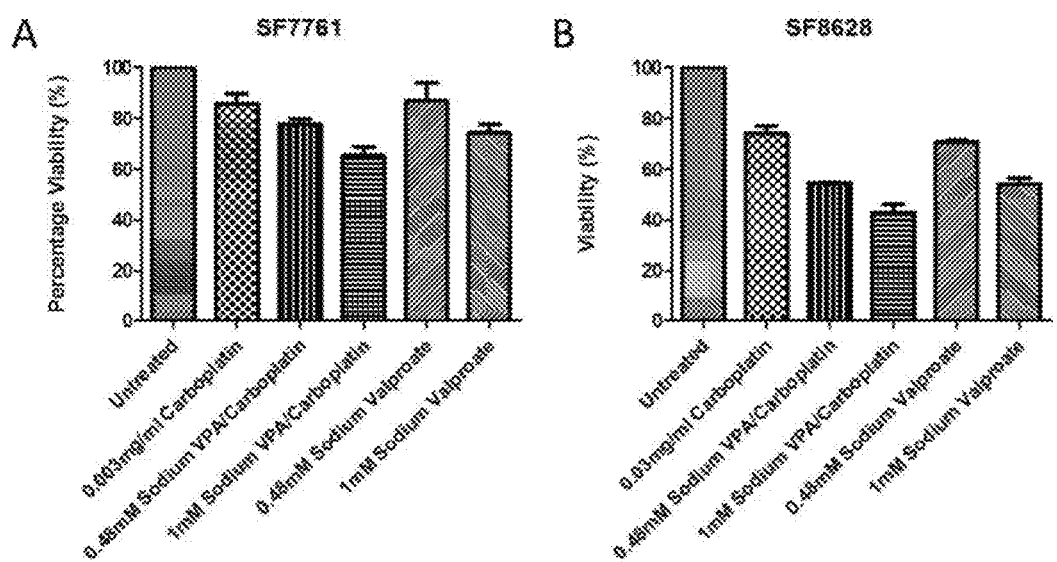
FIG. 7 shows that pre-dosing glioma cells with sodium valproate potentiates the cytotoxicity of carboplatin in glioma cells. Two glioma cell lines (A) SF7761 and (B) SF8628 were dosed with sodium valproate for 72 h, followed by 6 h of carboplatin, after which, the drug was washed out and given fresh sodium valproate. Proliferation was assessed by MTT assay, and results expressed as a % relative to the untreated control cells. (C) Using the combination index (CI) to establish if two drugs work synergistically or antagonistically, we demonstrated that pre-conditioning of cells with sodium valproate prior to carboplatin led to a CI value of below 1 for both glioma cell lines, indicative of synergy.
Figure 8:
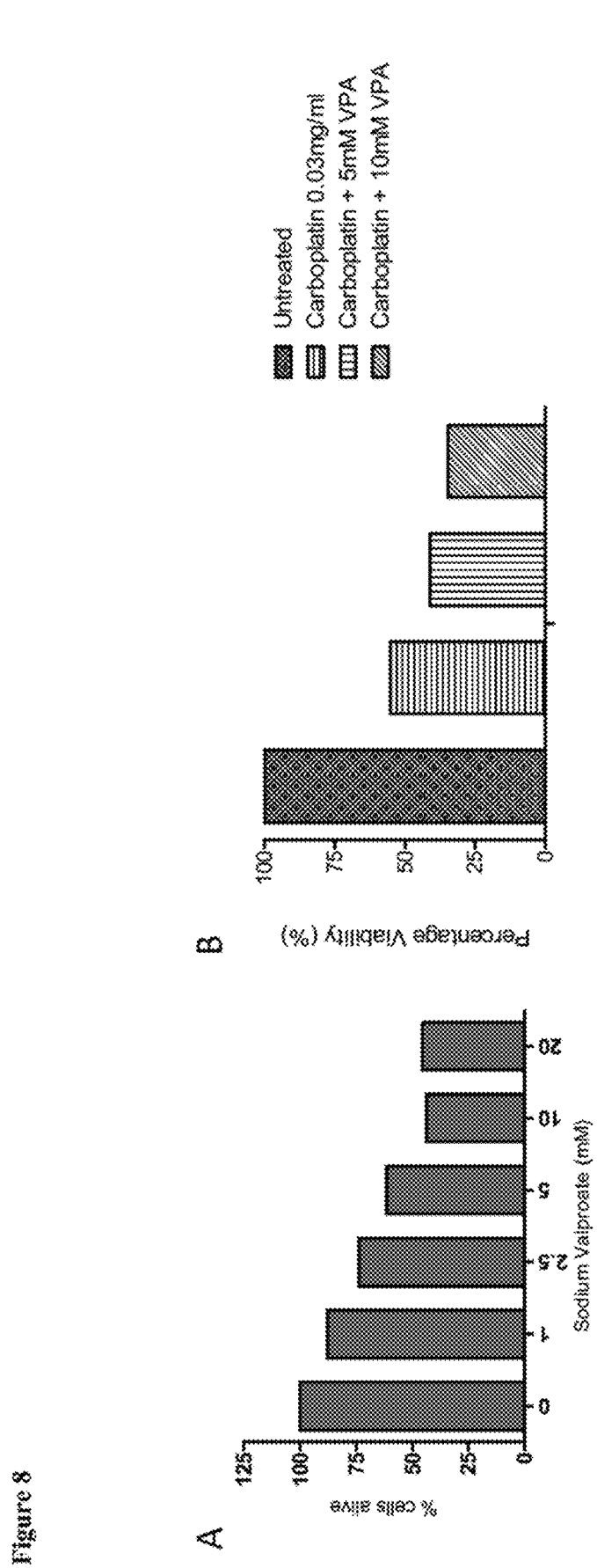
FIG. 8 shows 6 h sequential dosing of sodium valproate causes cytotoxicity to glioma cells, and combined 6 h sequential dosing with carboplatin enhances cytotoxicity compared to carboplatin alone. One glioma cell line thus far has been tested with (A) 6 h dosing of VPA repeated one two consecutive days, followed by assessment of proliferation by MTT. The results are expressed as % relative to control and demonstrate a dose dependent decrease in cell viability. (B) Combined dosing of carboplatin and sodium valproate for 6 h on two consecutive days demonstrates that when the two drugs are combined there is a greater decrease in cell viability compared with carboplatin alone.
Figure 9:
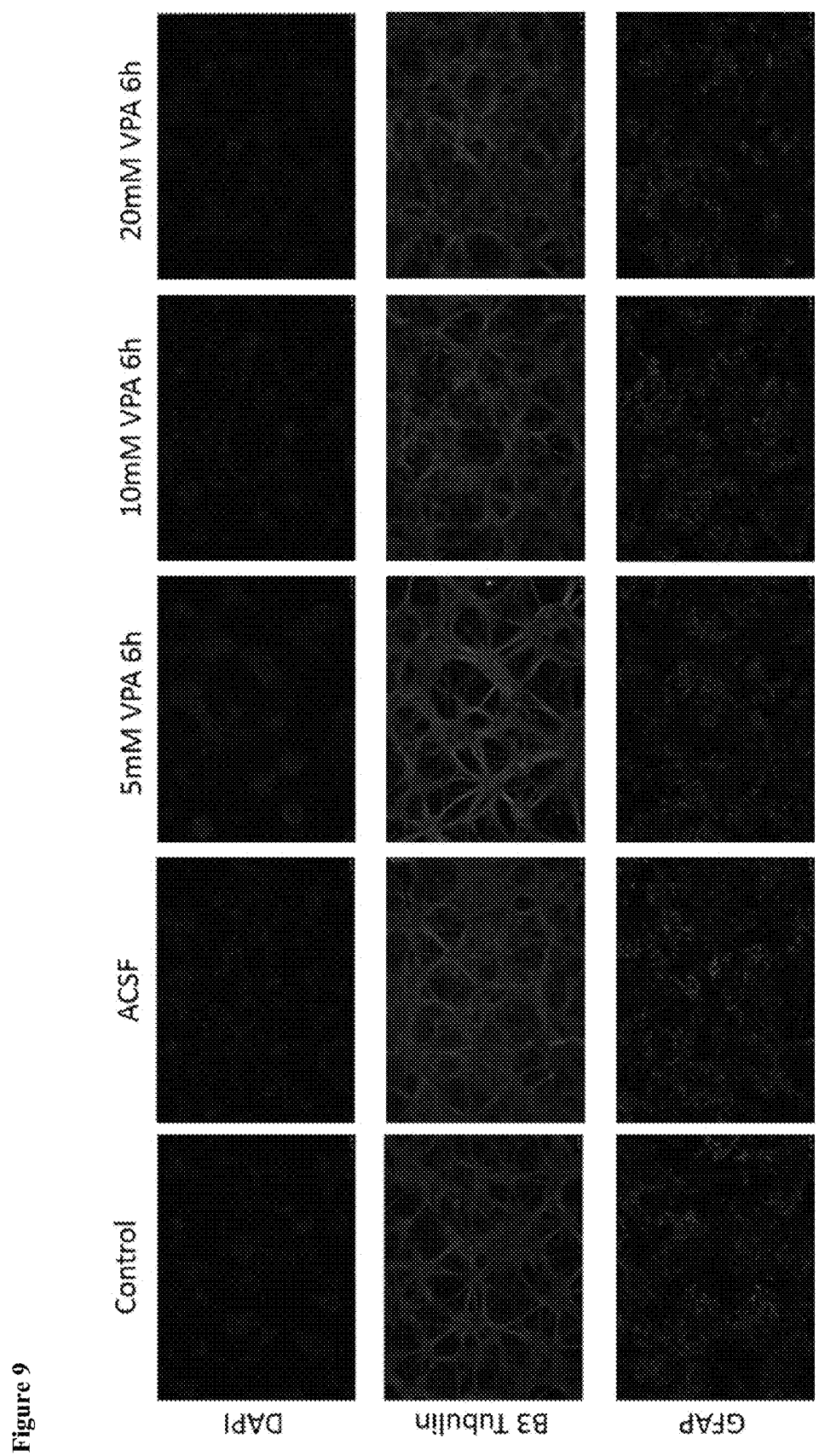
FIG. 9 shows 6 h dosing of normal hippocampal cultures demonstrates minimal neuronal toxicity when cells are dosed with sodium valproate for 6 h. Normal hippocampal cells were plated onto coverslips and grown for 72 h prior to dosing with sodium valproate to assess the toxicity of the drug against normal neuronal and glial cells. Cells were drugged with sodium valproate for 6 h, after which time the drug was washed off and fresh media added. Cells were further incubated for 72 h prior to fixing and staining with B3 tubulin (neuronal marker) and GFAP (glial cell marker) to determine to the toxicity of sodium valproate.

Example 2: Evaluation of In Vitro Cytotoxicity of Sodium Valproate for the Treatment of Malignant Glioma Aims
  Determine the in vitro cytotoxicity of sodium valproate in human glioma cell lines using a cell viability assay.
  Determine if sodium valproate potentiates the cytotoxicity of carboplatin on glioma cell lines.
  Investigate if sodium valproate causes glioma cell death after 6 h of drug exposure—a situation mimicking the clinical infusion time of drug delivered by convection enhanced delivery.
  Determine the in vitro toxicity of sodium valproate on primary normal hippocampal neurons and glial cells using immunofluorescence microscopy.
Results
  Sodium Valproate kills glioma cells in vitro in both commercial cell lines and ex vivo derived glioblastoma and DIPG (see FIG. 6).
  Pre-conditioning of cells with sodium valproate prior to carboplatin dosing potentiates the cytotoxicity of carboplatin. Furthermore, using an equation known as the combination index, we have demonstrated that pre-conditioning of cells with sodium valproate followed by carboplatin exposure synergistically enhanced the cytotoxicity (see FIG. 7).
  Short 6 hr exposures of sodium valproate which mimics the clinical infusion time of drug delivery by convection enhanced delivery demonstrates that high doses of sodium valproate kills glioma cells (see FIG. 8).
  Sodium valproate doesn't cause significant neuronal toxicity in normal primary hippocampal cultures when dosed for 6 h and then assayed 72 h after drugging. Some toxicity can be seen in the glial (non-neuronal supporting cells in the brain) at a concentration of 20 mM sodium valproate (see FIG. 9).
Conclusions
  Sodium valproate reduces the proliferation of glioma cells in vitro after both short (6 h) and long (72 h) drug exposure.
  Sodium valproate potentiated the cytotoxic effects of carboplatin on glioma cell lines.
  Sodium valproate does not significantly cause neuronal toxicity in primary normal brain cells.
  Intermittent CED of combined carboplatin and sodium valproate may provide a novel therapeutic combination for the treatment of patients with malignant glioma.

What is claimed is:
1. A method of treating a central nervous system (CNS) disorder, the method comprising administering an effective amount of a water-soluble histone deactylase inhibitor directly into a brain of a subject having the CNS disorder via convection enhanced delivery.

2. The method of treating a CNS disorder according to claim 1, wherein the water-soluble histone deacetylase inhibitor is a water or lipid soluble histone deacetylase inhibitor encapsulated in a lipid membrane or polymeric carrier.

3. The method of treating a CNS disorder according to claim 2, wherein the polymeric carrier is selected from the group consisting of a liposome, a micelle and a nanoparticle.

4. The method of treating a CNS disorder according to claim 2, wherein the lipid membrane or polymeric carrier is biodegradable and non-neurotoxic.

5. The method of treating a CNS disorder according to claim 2, wherein the lipid membrane or polymeric carrier has a diameter of less than 200 nm.

6. The method of treating a CNS disorder according to claim 2, wherein the lipid soluble histone deacetylase inhibitor is selected from one or more of the group consisting of panobinostat, Entinostat, Vorinostat, Mocetinostat, Romidepsin, Belinostat, Abexinostat, Givinostat, Resminostat, Quisinostat, Pracinostat, Pyroxamide, Tubacin and Trichostatin A.

7. The method of treating a CNS disorder according to claim 1, wherein the water-soluble histone deactylase inhibitor is selected from one or more of the group consisting of sodium valproate, sodium butyrate and dacinostat.

8. The method of treating a CNS disorder according to claim 1, wherein the water-soluble histone deacetylase inhibitor is administered daily for at least 1 day via convection enhanced delivery for a period in the range of 4 to 12 hours.

9. The method of treating a CNS disorder according to claim 8, wherein the water-soluble histone deacetylase inhibitor is administered daily for at least 2 days via convection enhanced delivery.

10. The method of treating a CNS disorder according to claim 8, wherein the water-soluble histone deacetylase inhibitor is administered in repeat cycles of 4 to 6 week intervals.

11. The method of treating a CNS disorder according to claim 1, wherein the water-soluble histone deacetylase inhibitor is administered in combination with a systemic dose of a same histone deacetylase inhibitor, and
the systemic dose is in a water-soluble or lipid soluble form.

12. The method of treating a CNS disorder according to claim 1, wherein the water-soluble histone deacetylase inhibitor is administered in combination with a chemotherapeutic agent or another water-soluble histone deacetylase inhibitor, and
the chemotherapeutic agent or other water-soluble histone deacetylase inhibitor is administered via convection enhanced delivery.

13. The method of treating a CNS disorder according to claim 12, wherein the chemotherapeutic agent is selected from one or more of the group consisting of carboplatin, topotecan, cisplatin, oxaliplatin, satraplatin, picoplatin, nedaplatin and triplatin.

14. The method of treating a CNS disorder according to claim 1, wherein the water-soluble histone deacetylase inhibitor is administered to the brain via intermittent convection enhanced delivery concurrently with a systemic therapy, the systemic therapy including a systemic dose including one or more component selected from the group consisting of temozolomide, bevacizumab and dexamethasone.

15. The method of treating a CNS disorder according to claim 1, wherein the water-soluble histone deacetylase inhibitor is administered to the brain via intermittent convection enhanced delivery concurrently with cranial radiotherapy including sterotactic radiotherapy.

16. The method of treating a CNS disorder according to claim 1, wherein the water-soluble histone deacetylase inhibitor is administered to the brain via intermittent convection enhanced delivery concurrently with an immune check point blockade.

17. The method of treating a CNS disorder according to claim 16, wherein the immune check point blockade includes one or more component selected from the group consisting of anti PD-1 antibody (nivolumab) and anti CTLA-4 antibody (ipilimumab).

18. The method of treating a CNS disorder according to claim 1, wherein the water-soluble histone deacetylase inhibitor is administered to the brain via intermittent convection enhanced delivery concurrently with immunotherapy by systemic glioma vaccination.

19. The method of treating a CNS disorder according to claim 1, wherein the CNS disorder is cancer.

20. The method of treating a CNS disorder according to claim 19, wherein the CNS disorder is brain cancer.

21. The method of treating a CNS disorder according to claim 20, wherein the CNS disorder is glioma.

22. The method of treating a CNS disorder according to claim 1, wherein the water-soluble histone deacetylase inhibitor is administered concurrently with systemic administration of a drug efflux inhibitor.

23. The method of treating a CNS disorder according to claim 22, wherein the drug efflux inhibitor is as least one selected from the group consisting of cyclosporin A, Verapamil, Quinidine, Dexverapamil, vaspodar, mitotane, lanquidar, and elecridar.

24. The method of treating a CNS disorder according to claim 1, wherein the water-soluble histone deacetylase inhibitor is administered at a concentration in the range of 2.5 mM to 10 mM.

* * * * *